(12) United States Patent
Bramucci et al.

(10) Patent No.: US 7,057,030 B2
(45) Date of Patent: Jun. 6, 2006

(54) RHODOCOCCUS GENE ENCODING ALDOXIME DEHYDRATASE

(75) Inventors: Michael G. Bramucci, Folsom, PA (US); Vasantha Nagarajan, Wilmington, DE (US); Mario W. Chen, Chadds Ford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 3 days.

(21) Appl. No.: 10/387,094

(22) Filed: Mar. 12, 2003

(65) Prior Publication Data

US 2003/0215929 A1    Nov. 20, 2003

Related U.S. Application Data

(60) Provisional application No. 60/365,019, filed on Mar. 15, 2002.

(51) Int. Cl.
*C07H 21/04*   (2006.01)
*C12N 1/20*    (2006.01)

(52) U.S. Cl. .................... 536/23.7; 536/23.1; 435/195; 435/252.3; 435/69.1; 435/254.2; 435/254.3

(58) Field of Classification Search ............... 536/23.1, 536/23.7; 435/252.3, 195, 69.1, 254.2, 254.3
See application file for complete search history.

(56) References Cited

U.S. PATENT DOCUMENTS

| 5,635,391 A | 6/1997 | Petre et al. |
| 5,648,256 A | 7/1997 | Yamada et al. |
| 5,811,286 A | 9/1998 | Fallon et al. |
| 2003/0215929 A1* | 11/2003 | Bramucci et al. ........... 435/128 |

FOREIGN PATENT DOCUMENTS

| WO | WO 01/75077 A2 | 10/2001 |
| WO | WO 02/12530 A2 | 2/2002 |

OTHER PUBLICATIONS

Yasuhisa Asano, et al., Overview of screening for new microbial catalysis and their uses in organic sythesis-selection and optimization of biocatalysts, Journal of Biotechnology, vol. 94. pp. 65-72, 2002.

National Center For Biotechnology Information General Identification No. 4126493, Accession No. AB016078, Feb. 25, 1999, M. Nojiri et. al., Functional Expression of Nitrile Hydratase in *Escherichia coli*.

Yasuo Kato et. al., A new enzymatic method of nitrile synthesis by *Rhodococcus* sp. strain YH3-3, Journal of Molecular Catalysis B: Enzymatic, vol. 6, pp. 249-256, 1999.

Yasuhisa Asano, Selection and Directed Evolution of New Microbial Biocatalysts and Their Application to Organic Synthesis, Agric.Chem. Biotechnol., vol. 43, pp. 207-210, 2000.

Hull et al., *Arabidopsis cytochrome* P450s that catalyze the first ste of tryptophan-dependent indole-3-acetic acid biosynthesis, PNAS USA, vol. 97: pp, 2379-2384, 2000.

Wittstock and Halkier, Cytochrome P450 CYP79A2 from *Arabidopsis thaliana* L. Catalyzes the Conversion of L-Phenylalanine to Phenylacetaldoxime in the Biosynthesis of Benzylglucosinolate, J. Biol. Chem, 275: 14659-14666, 2000.

Kato et al., Distribution of Aldoxime Dehydratase in Microorganisms, Appl. Environ. Microbiol., vol. 66: pp. 2290-2296, 2000.

Kato et al., Novel Heme-Containing Lyase, Phenylacetaldoxime Dehydratase from *Bacillus* sp. Strain OxB-1: Purification, Characterization, and Molecular Cloning of the Gene, Biochem, vol. 39: pp. 800-809, 2000.

Xie et al., High Yield Synthesis of Nitriles by a New Enzyme, Phenylacetaldoxime Dehydratase, from *Bacillus* sp. Strain OxB-1, Biosci. Biotechnol. Biochem., 65(12): pp. 2666-2672, 2001.

Kobayashi et al., Monohydrolysis of an Aliphatic Dinitrile Compound, Tetrahedron vol. 46, pp. 5587-5590, 1990.

Kobayashi et al., Purification and Characterization of a Novel Nitrilase of *Rhodococcus rhodochrous* K22 That Acts on Aliphatic Nitriles, J. Bacteriol. 172: pp. 4807-4815, 1990.

Cowan et al., Biochemistry and biotechnology of mesophilic and themophilic nitrile metabolizing enzymes, Extremophiles vol. 2, pp. 201-216, 1998.

* cited by examiner

*Primary Examiner*—Chih-Min Kam

(57) ABSTRACT

A gene has been isolated from a *Rhodococcus* sp. encoding an aldoxime dehydratase enzyme useful for the conversion of aldoxime substrates to nitrilases and other downstream intermediates. The gene has been cloned into a recombinant host and expressed.

8 Claims, 1 Drawing Sheet

SEQUENCE LISTING

```
<160> NUMBER OF SEQ ID NOS: 7
<210> SEQ ID NO 1
<211> LENGTH: 1125
<212> TYPE: DNA
<213> ORGANISM: Rhodococcus erythropolis AN12
<220> FEATURE:
<221> NAME/KEY: CDS
<222> LOCATION: (67)..(1125)

<400> SEQUENCE: 1
attttcggca cggcgttgcc aagtgccagg cacccgatcc gaccacctac atcacaggga      60
gcactc atg gaa tct gca atc ggt gaa cat ctt caa tgc ccg cgc acg     108
       Met Glu Ser Ala Ile Gly Glu His Leu Gln Cys Pro Arg Thr
         1               5                  10 ctg acc agg cgc gtt ccg gat acc tat tcg cca cca ttt ccc atg tgg     156
Leu Thr Arg Arg Val Pro Asp Thr Tyr Ser Pro Pro Phe Pro Met Trp
 15                  20                  25                  30 gtc ggg cgt gcg gac gac aca ttg cac cag gtc gcg atg ggc tat ctc     204
Val Gly Arg Ala Asp Asp Thr Leu His Gln Val Ala Met Gly Tyr Leu
                 35                  40                  45
```

```
ggc gtg cag ttc cgc ggc gag gat cag cgc tcg gca gca ctg cag tcc      252
Gly Val Gln Phe Arg Gly Glu Asp Gln Arg Ser Ala Ala Leu Gln Ser
             50                  55                  60
atg cgg gat atc gtc gcc ggc ttc gac ttg ccg gac gga ccg gca cac      300
Met Arg Asp Ile Val Ala Gly Phe Asp Leu Pro Asp Gly Pro Ala His
         65                  70                  75 cac gat ctg acc cac cac atc gac aac cag ggc tac gag aat ctg atc      348
His Asp Leu Thr His His Ile Asp Asn Gln Gly Tyr Glu Asn Leu Ile
     80                  85                  90
gtc gtc ggg tac tgg aaa gat gtt tct tcc caa cat cgt tgg agc aca      396
Val Val Gly Tyr Trp Lys Asp Val Ser Ser Gln His Arg Trp Ser Thr
 95                 100                 105                 110
tca gct ccg gtg gcc tcc tgg tgg gag tcc gag gac cgc ttg tcc gac      444
Ser Ala Pro Val Ala Ser Trp Trp Glu Ser Glu Asp Arg Leu Ser Asp
                115                 120                 125
gga ttg ggg ttc ttc cgg gag atc gtg gcc ccg aga gcc gaa caa ttc      492
Gly Leu Gly Phe Phe Arg Glu Ile Val Ala Pro Arg Ala Glu Gln Phe
            130                 135                 140 gaa acg ctc tac gcg ttc cag gac gat ctc ccc gga gtg gga gca gtc      540
Glu Thr Leu Tyr Ala Phe Gln Asp Asp Leu Pro Gly Val Gly Ala Val
        145                 150                 155
atg gac ggt gtc agc ggc gag atc aac gag cac ggc tac tgg ggt tcg      588
Met Asp Gly Val Ser Gly Glu Ile Asn Glu His Gly Tyr Trp Gly Ser
    160                 165                 170
atg cgc gag cgc ttt ccg atc tct cag acc gac tgg atg cag gcc tcg      636
Met Arg Glu Arg Phe Pro Ile Ser Gln Thr Asp Trp Met Gln Ala Ser 175                 180                 185                 190
ggc gaa cta cgg gtc gtc gcc ggt gac ccc gtc gca ggt gga cgc gta      684
Gly Glu Leu Arg Val Val Ala Gly Asp Pro Val Ala Gly Gly Arg Val
                195                 200                 205
gta gtg cgg ggg cac gac aac atc gca ctg atc aga tcc ggg cag gac      732
Val Val Arg Gly His Asp Asn Ile Ala Leu Ile Arg Ser Gly Gln Asp
            210                 215                 220
tgg gcc gac gcg gaa gcg gac gag cgc agc ctc tac ctg gac gaa atc      780
Trp Ala Asp Ala Glu Ala Asp Glu Arg Ser Leu Tyr Leu Asp Glu Ile
        225                 230                 235
ctg ccc act ctc caa tcg ggc atg gac ttc ctc cgc gac aac ggc ccg      828
Leu Pro Thr Leu Gln Ser Gly Met Asp Phe Leu Arg Asp Asn Gly Pro 240                 245                 250
gcc gtc ggg tgc tac agc aac cgt ttc gta cgc aat atc gac atc gac      876
Ala Val Gly Cys Tyr Ser Asn Arg Phe Val Arg Asn Ile Asp Ile Asp
255                 260                 265                 270
gga aac ttc ctc gac ctg agc tac aac atc ggt cac tgg gcc tca ctc      924
Gly Asn Phe Leu Asp Leu Ser Tyr Asn Ile Gly His Trp Ala Ser Leu
                275                 280                 285
gac caa ctc gag cgg tgg tcg gaa tcc cac ccg acc cat ctg cgg atc      972
Asp Gln Leu Glu Arg Trp Ser Glu Ser His Pro Thr His Leu Arg Ile
            290                 295                 300
ttc acg acg ttc ttc cgg gtc gcc gag ggc ctg tcg aaa tta cgt ctc     1020
Phe Thr Thr Phe Phe Arg Val Ala Glu Gly Leu Ser Lys Leu Arg Leu 305                 310                 315
tac cat gag gtc tcg gta ttc gat gcc gcc gat cag ctg tac gag tac     1068
Tyr His Glu Val Ser Val Phe Asp Ala Ala Asp Gln Leu Tyr Glu Tyr
    320                 325                 330 atc aac tgc cat ccc ggg acc ggg atg ctg cgc gac gcg gtg acc acc     1116
Ile Asn Cys His Pro Gly Thr Gly Met Leu Arg Asp Ala Val Thr Thr
335                 340                 345                 350
gcc gcg cac                                                         1125
Ala Ala His

<210> SEQ ID NO 2
<211> LENGTH: 353
<212> TYPE: PRT
```

<213> ORGANISM: Rhodococcus erythropolis AN12

<400> SEQUENCE: 2

```
Met Glu Ser Ala Ile Gly Glu His Leu Gln Cys Pro Arg Thr Leu Thr
1               5                   10                  15
Arg Arg Val Pro Asp Thr Tyr Ser Pro Pro Phe Pro Met Trp Val Gly
                20                  25                  30
Arg Ala Asp Asp Thr Leu His Gln Val Ala Met Gly Tyr Leu Gly Val
            35                  40                  45
Gln Phe Arg Gly Glu Asp Gln Arg Ser Ala Ala Leu Gln Ser Met Arg
        50                  55                  60
Asp Ile Val Ala Gly Phe Asp Leu Pro Asp Gly Pro Ala His His Asp
65                  70                  75                  80
Leu Thr His His Ile Asp Asn Gln Gly Tyr Glu Asn Leu Ile Val Val
                85                  90                  95
Gly Tyr Trp Lys Asp Val Ser Ser Gln His Arg Trp Ser Thr Ser Ala
                100                 105                 110
Pro Val Ala Ser Trp Trp Glu Ser Glu Asp Arg Leu Ser Asp Gly Leu
            115                 120                 125
Gly Phe Phe Arg Glu Ile Val Ala Pro Arg Ala Glu Gln Phe Glu Thr
        130                 135                 140
Leu Tyr Ala Phe Gln Asp Asp Leu Pro Gly Val Gly Ala Val Met Asp
145                 150                 155                 160
Gly Val Ser Gly Glu Ile Asn Glu His Gly Tyr Trp Gly Ser Met Arg
                165                 170                 175
Glu Arg Phe Pro Ile Ser Gln Thr Asp Trp Met Gln Ala Ser Gly Glu
            180                 185                 190
Leu Arg Val Val Ala Gly Asp Pro Val Ala Gly Arg Val Val Val
        195                 200                 205
Arg Gly His Asp Asn Ile Ala Leu Ile Arg Ser Gly Gln Asp Trp Ala
        210                 215                 220
Asp Ala Glu Ala Asp Glu Arg Ser Leu Tyr Leu Asp Glu Ile Leu Pro
225                 230                 235                 240
Thr Leu Gln Ser Gly Met Asp Phe Leu Arg Asp Asn Gly Pro Ala Val
                245                 250                 255
Gly Cys Tyr Ser Asn Arg Phe Val Arg Asn Ile Asp Ile Asp Gly Asn
            260                 265                 270
Phe Leu Asp Leu Ser Tyr Asn Ile Gly His Trp Ala Ser Leu Asp Gln
        275                 280                 285
Leu Glu Arg Trp Ser Glu Ser His Pro Thr His Leu Arg Ile Phe Thr
    290                 295                 300
Thr Phe Phe Arg Val Ala Glu Gly Leu Ser Lys Leu Arg Leu Tyr His
305                 310                 315                 320
Glu Val Ser Val Phe Asp Ala Ala Asp Gln Leu Tyr Glu Tyr Ile Asn
                325                 330                 335
Cys His Pro Gly Thr Gly Met Leu Arg Asp Ala Val Thr Thr Ala Ala
            340                 345                 350
His
```

<210> SEQ ID NO 3
<211> LENGTH: 19
<212> TYPE: DNA
<213> ORGANISM: artificial sequence
<220> FEATURE:
<223> OTHER INFORMATION: Primer HK12

```
<400> SEQUENCE: 3
gagtttgatc ctggctcag                                                      19

<210> SEQ ID NO 4
<211> LENGTH: 16
<212> TYPE: DNA
<213> ORGANISM: artificial sequence
<220> FEATURE:
<223> OTHER INFORMATION: Primer HK13

<400> SEQUENCE: 4
taccttgtta cgactt                                                         16

<210> SEQ ID NO 5
<211> LENGTH: 17
<212> TYPE: DNA
<213> ORGANISM: artificial sequence
<220> FEATURE:
<223> OTHER INFORMATION: Primer HK14
<220> FEATURE:
<221> NAME/KEY: misc_feature
<222> LOCATION: (11)..(11)
<223> OTHER INFORMATION: Y = C or T
<220> FEATURE:
<221> NAME/KEY: misc_feature
<222> LOCATION: (12)..(12)
<223> OTHER INFORMATION: M = A or C

<400> SEQUENCE: 5
gtgccagcag ymgcggt                                                        17

<210> SEQ ID NO 6
<211> LENGTH: 24
<212> TYPE: DNA
<213> ORGANISM: artificial sequence
<220> FEATURE:
<223> OTHER INFORMATION: Primer ALD-F

<400> SEQUENCE: 6
atggaatctg caatcggtga acat                                                24

<210> SEQ ID NO 7
<211> LENGTH: 24
<212> TYPE: DNA
<213> ORGANISM: artificial sequence
<220> FEATURE:
<223> OTHER INFORMATION: Primer ALD-R

<400> SEQUENCE: 7
gtgcgcggcg gtggtcaccg cgtc                                                24
```

RHODOCOCCUS GENE ENCODING ALDOXIME DEHYDRATASE

Figure 1:
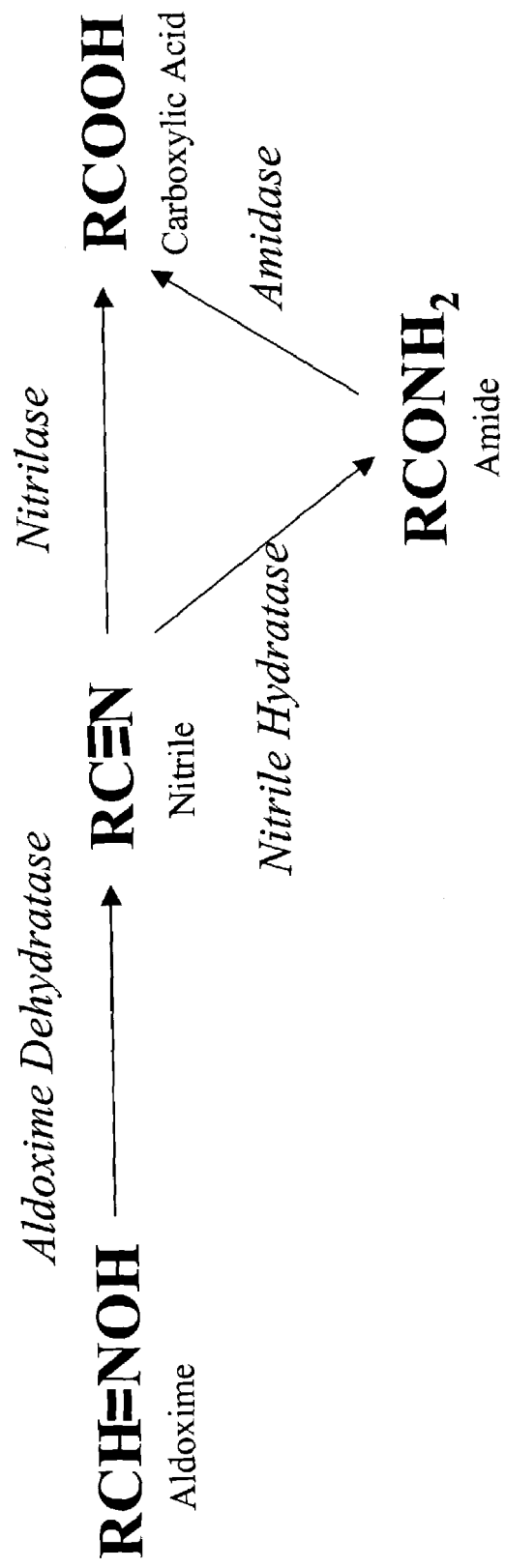

This application claims the benefit of U.S. Provisional Application, 60/365,019 filed Mar. 15, 2002.

FIELD OF THE INVENTION

The present invention relates to the fields of molecular biology, biocatalyst development and biotransformation of organic molecules. More specifically, the present invention relates to cloning and expression of a novel *Rhodococcus* gene encoding an aldoxime dehydratase enzyme.

BACKGROUND OF THE INVENTION

Aldoximes have the general chemical structure RHC=NOH where "R" is an aryl or alkyl group. Plants synthesize a variety of aldoximes as intermediates in biochemical pathways leading to compounds that are used as developmental signals and as defenses against pathogens (Hull et al., *PNAS USA*, 97:2379–84 (2000); Wittstock and Halkier, *J Biol Chem*, 275:14659–66 (2000)). A variety of microorganisms are known to degrade aldoximes (Kato et al., *Appl. Environ. Microbiol.*, 66:2290–2296 (2000)). Bacteria typically degrade aldoximes by first converting the aldoxime to a nitrile by means of aldoxime dehydratase and subsequently converting the nitrile to a carboxylic acid by means of nitrilase or a combination of nitrile hydratase and amidase (FIG. 1). The ability of plants to synthesize various aldoximes and the possibility of converting an aldoxime into a nitrile, amide or carboxylic acid make aldoximes potentially useful as starting materials or as intermediates in biotransformations.

One factor that limits the use of aldoximes in biotransformations is the lack of identified aldoxime dehydratase genes. In deed, only one aldoxime dehydratase gene is known in the literature (Kato et al., *Biochem* 39:800–809 (2000)). Although several strains of *Rhodococcus* and other bacteria that degrade aldoximes and have aldoxime dehydratase activity are described in the existing literature (Kato et al., *Appl. Environ. Micorbiol.*, 66:2290–2296 (2000)), with the exception of genes from *Bacillus*, the genes for aldoxime dehydratase in these bacteria are largely unknown. One report exists describing the cloning and expression of a gene encoding a phenylacetaldoxime dehydratase, from a *Bacillus sp.* strain OxB-1, and the recombinant production of arylalkyl and alkyl-nitriles from the corresponding aldoximes (Xie et al., *Biosci. Biotechnol. Biochem.*, 65(12): 2666–2672 (2001)).

The problem to be solved therefore is to identify new aldoxime dehydratase genes for use in the recombinant production of nitriles, amides, carboxylic acids, and downstream intermediates in the aldoxime-nitrile-carboxylic acid pathway.

Applicants have solved the stated problem by isolating the gene for aldoxime dehydratase (oxd) from a *Rhodococcus erythropolis* AN12 strain containing an open reading frame (ORF) that encodes aldoxime dehydratase and by expressing the *Rhodococcus* oxd gene in *E. coli*.

SUMMARY OF THE INVENTION

The present invention relates to an isolated nucleic acid molecule encoding an aldoxime dehydratase, selected from the group consisting of: (a) an isolated nucleic acid molecule encoding the amino acid sequence as set forth in SEQ ID NO:2; (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or an isolated nucleic acid fragment that is complementary to (a) or (b).

The invention additionally relates to an isolated nucleic acid molecule comprising a first nucleotide sequence encoding a polypeptide of at least 353 amino acids that has at least 60% identity and alternatively 70% identity based on the Smith-Waterman method of alignment when compared to a polypeptide have the sequence as set forth in SEQ ID NO:2 or a second nucleotide sequence comprising the complement of the first nucleotide sequence, wherein said enzyme has aldoxime dehydratase activity.

The invention additionally relates to polypeptides encoded by the genes of the invention, genetic chimera incorporating the genes of the invention, and recombinant host cells harboring the same.

The invention additionally relates to a method for the production of a nitrile comprising:
  a) providing an aldoxime substrate having the general formula of RHC=NOH, wherein R is alkyl or aryl;
  b) providing a transformed host cell comprising a nucleic acid fragment encoding the isolated nucleic acid molecule of the invention under the control of suitable regulatory sequences; and
  c) contacting the aldoxime substrate of (a) with the transformed host cell of (b) under suitable growth conditions whereby a nitrile is produced.

Similarly the invention relates to a method for the production of a carboxylic acid comprising:
  a) providing an aldoxime substrate having the general formula of RHC=NOH, wherein R is alkyl or aryl;
  b) providing a transformed host cell comprising:
    1) a nucleic acid fragment encoding the isolated nucleic acid molecule of the invention under the control of suitable regulatory sequences;
    2) either at least one gene expressing a nitrilase or a set of genes expressing both a nitrile hydratase and an amidase; and
  c) contacting the aldoxime substrate of (a) with the transformed host cell of (b) under suitable growth conditions whereby a carboxylic acid is produced.

In another embodiment the invention relates to a method for the production of an amide comprising:
  a) providing an aldoxime substrate having the general formula of RHC=NOH, wherein R is alkyl or aryl;
  b) providing a transformed host cell comprising:
    1) a nucleic acid fragment encoding the isolated nucleic acid molecule of the invention under the control of suitable regulatory sequences;
    2) at least one gene expressing a nitrile hydratase; and
  c) contacting the aldoxime substrate of (a) with the transformed host cell of (b) under suitable growth conditions whereby an amide is produced.

BRIEF DESCRIPTION OF THE DRAWINGS AND SEQUENCE DESCRIPTIONS

FIG. 1 Illustrates the aldoxime-nitrile-carboxylic acid pathway.

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 Nucleotide sequence of the ORF containing *Rhodococcus* AN12 aldoxime dehydratase (oxd) gene.

SEQ ID NO:2 The deduced amino acid sequence of the ORF containing *Rhodococcus* AN12 aldoxime dehydratase (oxd) gene.

SEQ ID NO:3 Primer used to sequence and to amplify 16S rRNA gene sequences in *Rhodococcus erythropolis* strain AN12 and is denoted as HK12.

SEQ ID NO:4 Primer used to sequence and to amplify 16S rRNA gene sequences in *Rhodococcus erythropolis* strain AN12 and is denoted as HK13.

SEQ ID NO:5 Primer used to initiate sequencing reactions for 16S rRNA gene sequences in *Rhodococcus erythropolis* strain AN12 and is denoted as HK14.

SEQ ID NO:6 First of a primer pair used to amplify aldoxime dehydratase gene (oxd) from *Rhodococcus erythropolis* strain AN12 and is denoted as ALD-F.

SEQ ID NO:7 Second of a primer pair used to amplify aldoxime dehydratase gene (oxd) from *Rhodococcus erythropolis* strain AN12 and is denoted as ALD-R.

DETAILED DESCRIPTION OF THE INVENTION

The present invention provides an isolated novel aldoxime dehydratase gene (oxd) from *Rhodococcus erythropolis* strain AN12 that catalyzes the enzymatic conversion of an aldoxime to a nitrile. An isolated nucleic acid molecule encoding aldoxime dehydratase was transformed and functionally expressed in *E. coli* strain DH5α. The functionality of the cloned enzyme was illustrated by providing a method for the conversion of acetaldoxime to acetonitrile. The enzyme has relatively low homology to the only reported example of an isolated and expressed aldoxime dehydratase from *Bacillus sp.* Strain OxB-1 (Table 1; 31% identity, 50% similarity).

The aldoxime-nitrile-carboxylic acid pathway (FIG. 1) represents an industrially useful pathway. Industrial microbial engineering of the pathway requires the use of an aldoxime dehydratase gene and its ability to be expressed in an organism commonly used as a production host. The Applicants have provide a novel oxd gene and have illustrated the ability to functionally express the gene in *E. coli*.

In this disclosure, a number of terms and abbreviations are used. The following definitions are provided.

"Open reading frame" is abbreviated ORF.

"Polymerase chain reaction" is abbreviated PCR.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The terms *"Rhodococcus erythropolis* strain AN12 oxd", "AN12 oxd", and "oxd" are used interchangeably and refer to the *Rhodococcus erythropolis* strain AN12 aldoxime dehydratase gene (SEQ ID NO:1).

The term "aldoxime dehydratase" refers to an enzyme that catalyzes the dehydration of aldoximes (RHC=NOH) to form the corresponding nitriles (RC≡N) where "R" is an alkyl or aryl group.

The term "aldoxime substrate" refers to any suitable substrate for the aldoxime dehydratase of the invention. One typical substrate is acetaldoxime.

The term "aryl" means a univalent aromatic hydrocarbon

The term "alkyl" means a univalent group derived from alkanes by removal of a hydrogen atom from any carbon atom: $C_nH_{2n+1}$—. The groups derived by removal of a hydrogen atom from a terminal carbon atom of unbranched alkanes form a subclass of normal alkyl (n-alkyl) groups: $H[CH_2]_n$—. The groups $RCH_2$—, $R_2CH$— (R not equal to H), and $R_3C$— (R not equal to H) are primary, secondary, and tertiary alkyl groups, respectively.

The terms *"Rhodococcus erythropolis* AN12" or "AN12" are used interchangeably and refer to the *Rhodococcus erythropolis* AN12 strain.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. For example, a common set of stringent conditions consists of hybridization at 0.1×SSC, 0.1% SDS, 65° C. and washed with 2×SSC, 0.1% SDS followed by 0.1×SSC, 0.1% SDS. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses 0.1×SSC, 0.1% SDS, 65° C. for hybridization and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.*, 215: 403–410 (1990)). In general, a sequence of ten or more contiguous amino acids or thirty or more nucleotides is necessary to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics-computing suite (DNASTAR Inc., Madison, Wis.). Multiple alignment of the sequences may be performed using the CLUSTAL method of alignment (Higgins and Sharp, *CABIOS.*, 5:151–153 (1989)) with the default parameters (GAP PENALTY=10, GAP LENGTH PENALTY=10). Default parameters typically used for pairwise alignments using the CLUSTAL method are KTUPLE 1, GAP PENALTY=3, WINDOW=5, and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptide as set forth in SEQ ID NO:2. The skilled artisan is well aware of the "condon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site, and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to anitsense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically-stable inheritance. Host organisms containing the transformed nucleic acid fragments are referred to as "transgenic", "recombinant", or "transformed" organisms.

The term "carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The terms "plasmid", "vector", and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software packages include, but are not limited to, the GCG suite of programs (Wisconsin Package Version 9.0, Genetics Computer Group (GCG)), BLASTP, BLASTN, BLASTX (Altschul et al., *J. Mol. Biol.* 215:403–410 (1990)), DNAS-TAR (DNASTAR, Inc.), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). The term "MEME" refers to a software program used identify conserved diagnostic motifs based on hidden Markov model (Bailey and Elkan, *Fitting a mixture model by expectation maximization to discover motifs in biopolymers*, Proceedings of the Second International Conference on Intelligent Systems for Molecular Biology, pp. 28–36, AAAI Press, Menlo Park, Calif., 1994.) "MAST" (Bailey and Gribskov, *Bioinformatics*, 14:48–54 (1998)) is a program that takes the output from the MEME program and searches the identified motifs against the protein databases such as EMBL and SwissProt. Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Maniatis and by Silhavy, T. J., Bennan, M. L. and Enquist, L. W., *Experiments with Gene Fusions*, Cold Spring Harbor Laboratory Cold Press Spring Harbor, NY (1984) (hereinafter "Silhavy"); and by Ausubel, F. M. et al., *Current Protocols in Molecular Biology*, published by Greene Publishing Assoc. and Wiley-Interscience (1987)(hereinafter "Ausubel").

The present invention provides a newly discovered oxd gene isolated from *Rhodococcus* and encoding an aldoxime dehydratase enzyme which selectively catalyzes the hydrolysis of an aldoxime to the corresponding nitrile.

Sequence Identification

Comparison of the present oxd nucleotide sequence (SEQ ID NO:1) and deduced amino acid sequence (SEQ ID NO:2) to public databases reveals that the most similar known sequence is about 31% identical to the amino acid sequence reported herein (Xie et al., supra). The present open reading frame is 353 amino acids in length and has been expressed and demonstrated to have aldoxime dehydratase activity. Accordingly, it is within the scope of the present invention to provide an isolated nucleic acid molecule comprising a first nucleotide sequence encoding a polypeptide of at least 353 amino acids that has at least 60% identity based on the Smith-Waterman method of alignment (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.), when compared to a polypeptide have the sequence as set forth in SEQ ID NO:2 or a second nucleotide sequence comprising the complement of the first nucleotide sequence, wherein said enzyme has aldoxime dehydratase activity. More preferred amino acid fragments are at least about 70%–80% identical to the sequences herein. Most preferred are nucleic acid fragments that are at least about 80%–90% identical and particularly preferred sequences are 95% identical to the amino acid fragments reported herein. Similarly, preferred oxd encoding nucleic acid sequences encoding active proteins are those that are at least 70%–80% identical to the nucleic acid sequences of reported herein. More preferred oxd nucleic acid fragments are at least 80%–90% identical to the sequences herein. Most preferred are oxd nucleic acid fragments that are at least 95% identical to the nucleic acid fragments reported herein.

Isolation of oxd Homologs

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor et al., *PNAS* USA 82:1074 (1985)) or strand displacement amplification (SDA, Walker et al., *PNAS U.S.A.*, 89:392 (1992)).

For example, genes encoding similar proteins or polypeptides to those of the instant invention could be isolated directly by using all or a portion of the instant nucleic acid fragments as DNA hybridization probes to screen libraries from any desired bacteria is methodology well-known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify portions of the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and reproducible replication of the target nucleic acid. Methods of PCR primer design are common and well-known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.); Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)Generally, two short segments of the instant sequence may be used in polymerase chain reaction protocols to amplify longer nucleic acid fragments encoding homologous genes from DNA or RNA.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (GibcoBRL-Life Technologies, Rockville, Md.), specific 3' or 5' cDNA fragments can be isolated (Ohara et al., *PNAS USA*, 86:5673 (1989); Loh et al., *Science*, 243:217 (1989)).

Alternatively, the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single-stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.*, 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers, such as sodium citrate, Tris-HCl, PIPES or HEPES (pH range about 6–9), about 0.05 to 0.2% detergent, such as sodium dodecylsulfate, or between 0.05–20 mM EDTA, FICOLL (about 300–500 kilodaltons), polyvinylpyrrolidone (about 250–500 kdal), and serum albumin. Also included in the typical hybridization solution will be unlabeled carrier nucleic acids from about 1.0 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Recombinant Expression-Microbial

The gene and gene product of the instant sequences may be produced in heterologous host cells, particularly in the cells of microbial hosts. Expression in recombinant microbial hosts may be useful for the expression of various pathway intermediates; for the modulation of pathways already existing in the host for the synthesis of new products heretofore not possible using the host.

Preferred heterologous host cells for expression of the instant genes and nucleic acid fragments are microbial hosts that can be found broadly within the fungal or bacterial families that grow over a wide range of temperature, pH values, and solvent tolerances. For example, it is contemplated that any bacteria, yeast, or filamentous fungi will be suitable hosts for expression of the present nucleic acid fragments. Because of transcription, translation, and the protein biosynthetic apparatus is the same in the microbial hosts, functional genes can be expressed and used to generate cellular biomass, irrespective of the cellular feedstock. Large-scale microbial growth and functional gene expression may utilize a wide range of simple or complex carbohydrates, organic acids and alcohols, and saturated hydrocarbons such as methane or carbon dioxide in the case of photosynthetic or chemoautotrophic hosts. However, the functional genes may be regulated, repressed, or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to, bacterial, fungal, and yeast species such as *Aspergillus, Trichoderma, Saccharomyces, Pichia, Candida, Hansenula*, and bacteria such as *Salmonella, Bacillus, Acinetobacter, Zymomonas, Agrobacterium, Erythrobacter Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Methylobacterium, Alcaligenes, Synechocystis, Synechococcus, Anabaena, Thiobacillus, Methanobacterium, Klebsiella, Myxococcus*, and *Staphylococcus*.

Microbial expression systems and expression vectors containing regulatory sequences that direct high-level expression of foreign proteins are well known to those skilled in the art. Any of these could be used to construct chimeric genes for expression of present aldoxime dehydratase. These chimeric genes could then be introduced into appropriate microorganisms via transformation to provide high-level expression of the enzymes Accordingly, it is expected that introduction of chimeric genes encoding the instant bacterial enzyme under the control of the appropriate promoter will demonstarte increased aldoxime to nitrile conversion. It is contemplated that it will be useful to express the instant gene both in natural host cells as well as heterologous hosts. Introduction of the present oxd gene into native hosts will result in altered levels of existing aldoxime dehydratase activity. Additionally, the instant gene may also be introduced into non-native host bacteria where the existing aldoxime-nitrile pathway (FIG. 1) may be manipulated.

It has been demonstrated that the class of aldoxime dehydratases to which the present enzyme belongs has a broad substrate specificity (Kato et al., *Appl. Environ. Microbiol.*, 66:2290–2296 (2000)). Accordingly, in addition to the production of acetonitrile from acetaldoxime as demonstrated herein, it is expected that the present dehydratase will additionally act on other alkyl or aryl-alkyl aldoxime substrates to produce the corresponding nitrile including, but not limited to, acetaldoxime, Z-3-phenylpropionaldoxime, E-pyridine-3-aldoxime, Z-phenylacetaldoxime, Z-3-phenyl-propionaldoxime, E/Z-4-phenylbutyraldoxime, Z-p-chlorophenylacetaldoxime, Z-p-methoxyphenylacetaldoxime, E/Z-indoleacetaldoxime, Z-naphthacetaldoxime, E/Z-propionaldoxime, E/Z-n-butyraldoxime, E/Z-n-valeraldoxime, E/Z-isovaleraldoxime, E/Z-n-capronaldoxime, E/Z-isocapronaldoxime, E/Z-2-phenylpropionaldoxime, E/Z-cinnamaldehyde oxime, E/Z-p-hydroxyphenylacetaldoxime, Z-p-toluacetaldoxime, E/Z-thiophene-2-acetaldoxime, E/Z-diphenylacetaldoxime, and E/Z-mandelaldoxime, E-benzaldoxime, E-p-chlorobenzaldoxime, E-p-tolualdoxime, E-1-naphthoaldoxime, E-furfurylaldoxime, E-thiophene-2-carboxaldoxime, E-anisaldoxime, E-indole-3-carboxaldehyde oxime, E-quinoline-2-carboxaldehyde oxime, E-terephthalaldehyde oxime, E-isoph-thalaldehyde oxime, and E-pyrazinecarboxaldoxime, E/Z-isobutyraldoxime, Z-crotonaldoxime, E/Z-methacrylaldoxime, E/Z-cyclohexanecarboxaldehyde oxime; and Z-phenylacetaldoxime derivatives, such as E/Z-O-methyl phenylacetaldoxime, E/Z-O-benzyl phenylacetaldoxime, E-phenylacetaldehyde hydrazone, E/Z-O-acetyl-phenylacetaldoxime, E/Z-phenylacetone oxime, and E/Z-acetophenone oxime.

Vectors or cassettes useful for the transformation of suitable host cells are well known in the art. Typically, the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, IP$_L$, IP$_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

Knowledge of the sequence of the present gene will be useful in manipulating the aldoxime-nitrile-carboxylic acid pathway (FIG. 1), in any organism having such a pathway. Such manipulation may be desirable, not only for the increased production or nitriles, but also for the production of certain downstream intermediates such as carboxylic acids and amides. As is seen in FIG. 1, where bioconversion of an aldoxime to the corresponding carboxylic acid is desired, it may be necessary to up-regulate either the appropriate nitrilase or a combination of the appropriate nitrile hydratase and amidase for such a conversion. This is because the carboxylic acid may be derived either from the nitrile or the amide. Where production of an amide corresponding to an aldoxime is desired, up-regulation of the nitrile hydratase maybe necessary and, if accumulation of the amide is desired, disruption of the gene encoding the amidase may also be needed.

Accordingly it is an object of the present invention to provide a method for the production of a nitrile comprising:
  a) providing an aldoxime substrate having the general formula of RHC=NOH, wherein R is alkyl or aryl;
  b) providing a transformed host cell comprising a nucleic acid fragment encoding the isolated nucleic acid molecule of the invention under the control of suitable regulatory sequences; and
  c) contacting the aldoxime substrate of (a) with the transformed host cell of (b) under suitable growth conditions whereby a nitrile is produced.

Similarly it is an object of the invention to provide a method for the production of a carboxylic acid comprising:
  a) providing an aldoxime substrate having the general formula of RHC=NOH, wherein R is alkyl or aryl;
  b) providing a transformed host cell comprising:
    1) a nucleic acid fragment encoding the isolated nucleic acid molecule of the invention under the control of suitable regulatory sequences;
    2) either at least one gene expressing a nitrilase or a set of genes expressing both a nitrile hydratase and an amidase; and
  c) contacting the aldoxime substrate of (a) with the transformed host cell of (b) under suitable growth conditions whereby a carboxylic acid is produced.

Additionally it is an object of the invention to provide a method for the production of an amide comprising:
  a) providing an aldoxime substrate having the general formula of RHC=NOH, wherein R is alkyl or aryl;
  b) providing a transformed host cell comprising:
    1) a nucleic acid fragment encoding the isolated nucleic acid molecule of the invention under the control of suitable regulatory sequences;
    2) at least one gene expressing a nitrile hydratase; and
  c) contacting the aldoxime substrate of (a) with the transformed host cell of (b) under suitable growth conditions whereby an amide is produced.

Methods of manipulating genetic pathways are common and well known in the art. Selected genes in a particularly pathway may be up-regulated or down regulated by variety of methods. Additionally, competing pathways organism may be eliminated or sublimated by gene disruption and similar techniques.

Once a key genetic pathway has been identified and sequenced, specific genes may be up-regulated to increase the output of the pathway. For example, additional copies of the targeted genes may be introduced into the host cell on multicopy plasmids such as pBR322. Alternatively, the target genes may be modified so as to be under the control of non-native promoters. Where it is desired that a pathway operate at a particular point in a cell cycle or during a fermentation run, regulated or inducible promoter may used to replace the native promoter of the target gene. Similarly, in some cases the native or endogenous promoter may be modified to increase gene expression. For example, endogenous promoters can be altered in vivo by mutation, deletion, and/or substitution (U.S. Pat. No. 5,565,350; PCT/US93/03868).

Alternatively, it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods of gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (Hamilton et al., *J. Bacteriol.*, 171:4617–4622 (1989); Balbas et al., *Gene*, 136:211–213 (1993); Gueldener et al., *Nucleic Acids Res.*, 24:2519–2524 (1996); and Smith et al., *Methods Mol. Cell. Biol.*, 5:270–277 (1996))

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of anitsense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauser Associates, Inc., Sunderland, Mass., or Deshpande, Mukund V., *Appl. Biochem. Biotechnol.*, 36:227 (1992) (hereinafter "Brock").

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass. based upon the bacterial transposon Tn7; and the EZ::TN Transposon Insertion Systems, available from Epicentre Techologies, Madison, Wis., based upon the Tn5 bacterial transposable element).

Industrial Production

Where commercial production of nitriles is desired using the present oxd gene, a variety of culture methodologies may be applied. For example, large-scale production of a specific gene product over-expressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen, and the partial pressure of waste gases such as $CO_2$. Batch and Fed-Batch culturing methods are common and well known in the art and examples may be found in Brock.

Commercial production of nitriles (or the corresponding amide or carboxylic acid derivatives) from aldoximes may also be accomplished with a continuous culture. Continuous cultures are an open system where a defined culture media is added continuously to a bioreactor and an equal amount of conditioned media is removed simultaneously for processing. Continuous cultures generally maintain the cells at a constant high-liquid-phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, methane or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeast are known to utilize the carbon from methylamine to form trehalose or glycerol (Bellion et at., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485–489 (1990)). It is contemplated that the source of carbon utilized in the present invention may encompass a wide variety of carbon containing substrates and will only be limited by the choice of organism.

Recombinant Expression-Plants

Plants and algae are also known to produce aldoxime compounds. The nucleic acid fragments of the instant invention may be used to create transgenic plants having the ability to express the microbial protein. Preferred plant hosts will be any variety that will support a high production level of the instant proteins. Suitable green plants will include but are not limited to soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago sativa*), wheat (*Triticum sp*), barley (*Hordeum vulgare*), oats (*Avena sativa, L*), sorghum (*Sorghum bicolor*), rice (*Oryza sativa*), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, but are not limited to, commercially significant hosts such as *Spirulina, Haemotacoccus*, and *Dunalliela*. Production of nitrile compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences or the present invention should be capable of promoting expression of the present gene product. High-level plant promoters that may be used in this invention include the promoter of the small subunit (ss) of the ribulose-1,5-bisphosphate carboxylase from example from soybean (Berry-Lowe et al., *J. Mol. App. Gen.*, 1:483–498 (1982)), and the promoter of the chlorophyll a/b binding protein. These two promoters are known to be light-induced in plant cells (*Genetic Engineering of Plants, an Agricultural Perspective*, A. Cashmore, Plenum, N.Y. (1983), pages 29–38; Coruzzi et al., *J. Biol. Chem.*, 258:1399 (1983); and Dunsmuir et al., *J. Mol. App. Gen.*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.*, 4:2411–2418 (1985); De Almeida et al., *Mol. Gen. Genetics* 218:78–86 (1989)), and thus that multiple events must be screened in order to obtain lines displaying the desired expression level and pattern. Such screening may be accomplished by Southern analysis of DNA blots (Southern et al., *J. Mol. Biol.* 98:503 (1975)). Northern analysis of mRNA expression (Kroczek, R., *J. Chromatogr.*, 618(1–2): 133–145 (1993)), Western analysis of protein expression, or phenotypic analysis.

For some applications it will be useful to direct the instant protein to different cellular compartments. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J., *Ann. Rev. Plant Phys. Plant Mol. Biol.*, 42:21–53 (1991)), or nuclear localization signals (Raikhel, N., *Plant Phys.*, 100: 1627–1632 (1992)) added and/or with targeting sequences that are already present removed. While the references cited give examples of each of these, the list is not exhaustive and more targeting signals of utility may be discovered in the future that are useful in the invention.

Protein Engineering

It is contemplated that the present nucleotide may be used to produce gene products having enhanced or altered activity. Various methods are known for mutating a native gene sequence to produce a gene product with altered or enhanced activity including but not limited to error prone PCR (Melnikov et al., *Nucl. Acids Res.*, 27(4):1056–1062 (1999)); site directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. No. 5,605,793; U.S. Pat. No. 5,811,238; U.S. Pat. No. 5,830,721; and U.S. Pat. No. 5,837,458, incorporated herein by reference).

The method of gene shuffling is particularly attractive due to its facile implementation, high rate of mutagenesis, and ease of screening. The process of gene shuffling involves the restriction endonuclease cleavage of a gene of interest into fragments of specific size in the presence of additional populations of DNA regions having both similarity or difference to the gene of interest. This pool of fragments will then be denatured and reannealed to create a mutated gene. The mutated gene is then screened for altered activity.

The instant microbial sequence of the present invention may be mutated and screened for altered or enhanced activity by this method. The sequences should be double stranded and can be of various lengths ranging form 50 bp to 10 kb. The sequences may be randomly digested into fragments ranging from about 10 to 1000 bp, using restriction endonucleases well known in the art (Maniatis). In addition to the instant microbial sequences, populations of fragments that are hybridizable to all or portions of the microbial sequence may be added. Similarly, a population of fragments which are not hybridizable to the instant sequence may also be added. Typically, these additional fragment populations are added in about a 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation, and incubation in the presence of polymerase is repeated for a desired number to times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocol (Maniatis).

Furthermore, a hybrid protein can be assembled by fusion of functional domains using the gene shuffling (exon shuffling) method (Nixon et al., *PNAS*, 94:1069–1073 (1997)). The functional domain of the instant gene can be combined with the functional domain of other genes to create novel enzymes with desired catalytic function. A hybrid enzyme may be constructed using PCR overlap extension method and cloned into the various expression vectors using the techniques well known to those skilled in art.

Description of the Preferred Embodiments

The original environmental sample containing *Rhodococcus erythropolis* AN12 strain was obtained from a wastewater treatment facility. One milliliter of activated sludge was inoculated directly into 10 mL of S12 medium. Aniline was used as the sole source of carbon and energy. The culture was maintained by addition of 100-ppm aniline every 2–3 days. The culture was diluted (1:100 dilution) every 14 days. Bacteria that utilized aniline as a sole source of carbon and energy were isolated from the enrichment culture (Example 1).

The 16s rRNA gene of each isolate was PCR amplified and sequenced. The 16s rRNA gene sequence was used as the query sequence for a BLAST search (Altschul et al., *Nucleic Acids Res.*, 25:3389–3402 (1997)). BLAST results using the 16s rRNA gene indicated that strain AN12 was at least 98% similar to the 16s rRNA gene sequence of high G+C Gram positive bacteria belonging to the genus *Rhodococcus* (Example 1).

The *Rhodococcus erythropolis* strain AN12 genomic DNA was isolated and sequenced (Example 2). The oxd ORF was idnetified by conducting BLASTN searches form similarity to sequences contained in the BLAST non-redundant ("nr") database. Analysis identified a single sequence having 31% identity and 50% similarity to the oxd ORF from *R. erythropolis* strain AN12 (Table 1). The identified sequence was a phenylacetaldoxime dehydratase from *Bacillus sp.* OxB-1. The analysis suggested that the Applicants' novel gene may have aldoxime dehydratase activity.

In another embodiment, the Applicants cloned the oxd ORF sequence from *R. erythropolis* strain AN12 into an *E. coli* expression vector (Example 4). A 1,058 bp fragment (SEQ ID NO:3) was PCR amplified. The PCR product was then purified and inserted into a plasmid. The plasmid was used to transform *Escherichia coli* DH5α cells. Transformants were selected with ampicillin in LBamp agar. Plasmids from each transformant were isolated and analyzed via restriction fragment analysis in order to confirm the orientation of the oxd insert. Two strains were selected, one containing the oxd insert in the forward orientation (pMC552) and the other in the reverse orientation (pMC553).

In another embodiment, expression of oxd in *E. coli* DH5α was confirmed by culturing the *E. coli* strains DH5α pMC552 and DH5α pMC553 in 100-ppm acetaldoxime (Example 5, Table 2). Analytical samples were removed from the cultures at various time and analyzed by GC/FID for the presence of acetonitrile. *E. coli* DH5α pMC552, which contained the oxd insert in forward orientation, produced acetonitrile while DH5α pMC553 did not. The data indicates that the oxd gene is a functional aldoxime dehydratase.

In another embodiment, nitrilase and nitrile hydratase/amidase have been identified for a variety of important industrial applications involving the conversion of nitriles to the corresponding carboxylic acid. Numerous examples of isolated nitrilases, nitrile hydratases, and amidases, including examples of industrial use, are known in the art (WO 01/75077; WO 02/12530; U.S. Pat. No. 5,635,391; U.S. Pat. No. 5,648,256; U.S. Pat. No. 5,811,286; Kobayashi et al., Tetrahedron 46:5587–5590 (1990); Kobayashi et al., *J. Bacteriol.* 172:4807–4815 (1990); and Cowan et al., *Extremophiles* 2:201–216 (1998)). Additionally, when nitrile production is preferred, the nitrilase and nitrile hydratase/amidase enzymes can be inactivated so that the host organisms can accumulate nitrile. Aldoximes have been identified and are know to be precursors for a variety of important biosynthetic molecules. It has recently come to light the aldoxime dehydratases are also known to be closely linked to nitrilase activity in a variety of organisms. It appears that aldoxime to nitrile conversion is part of a larger biosynthetic pathway which converts aldoximes to nitriles and then to carboxylic acids.

Production of industrially useful nitriles, such as acetonitrile, from their corresponding aldoximes represents an important biochemical pathway. The pathway can be expanded to include carboxylic acids as it is know in the art that organisms having aldoxime dehydratase activity tend to also contain functional nitrilase or a combination of nitrile hydratase and amidase activities (Kato et al., *Appl. Environ. Microbiol.*, 66:2290–2296 (2000)). In another embodiment, the Applicants' novel aldoxime dehydratase can be used to transform a host cell used in the production of nitriles or the corresponding carboxylic acids.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Maniatis, Silhavy, and Ausubel.

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or in Brock. All reagents, restriction enzymes and materials used for the growth and maintenance of bacterial cells were obtained from DIFCO Laboratories (Bedford, Mass.), GIBCO™ Invitrogen Corp (Carlsbad, Calif.), or Sigma-Aldrich Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. Multiple alignments were created using the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "sec" means second(s), "d" means day(s), "µL" mean microliters, "mL" means milliliters, "µM" mean micromolar, "mM" mean millimolar, "ppm" means parts per million, "L" means liters.

EXAMPLE 1

Isolation and Characterization of Strain AN12

Example 1 describes the isolation of strain AN12 of *Rhodococcus erythropolis* on the basis of being able to grow on aniline as the sole source of carbon and energy. Analysis of a 16S rRNA gene sequence indicated that strain AN12 was related to high G+C Gram positive bacteria belonging to the genus *Rhodococcus*.

Bacteria that grew on aniline were isolated from an enrichment culture. The enrichment culture was established by inoculating 1 mL of activated sludge into 10 mL of S12 medium (10 mM ammonium sulfate, 50 mM potassium phosphate buffer (pH 7.0), 2 mM $MgCl_2$, 0.7 mM $CaCl_2$, 50 µM $MnCl_2$, 1 µM $FeCl_3$, 1 µM $ZnCl_3$, 1.72 µM $CuSO_4$, 2.53 µM $CoCl_2$, 2.42 µM $Na_2MoO_2$, and 0.0001% $FeSO_4$) in a 125 mL screw cap Erlenmeyer flask. The activated sludge was obtained from a wastewater treatment facility. The enrichment culture was supplemented with 100 ppm aniline added directly to the culture medium and was incubated at 25° C. with reciprocal shaking. The enrichment culture was maintained by adding 100 ppm of aniline every 2–3 days. The culture was diluted every 14 days by replacing 9.9 mL of the culture with the same volume of S12 medium. Bacteria that utilized aniline as a sole source of carbon and energy were isolated by spreading samples of the enrichment culture onto S12 agar. Aniline (5 µL) was placed on the interior of each Petri dish lid. The Petri dishes were sealed with parafilm and incubated upside down at room temperature (approximately 25° C.). Representative bacterial colonies were then tested for the ability to use aniline as a sole source of carbon and energy. Colonies were transferred from the original S12 agar plates used for initial isolation to new S12 agar plates and supplied with aniline on the interior of each Petri dish lid. The Petri dishes were sealed with parafilm and incubated upside down at room temperature (approximately 25° C.).

The 16S rRNA genes of each isolate were amplified by PCR and analyzed as follows. Each isolate was grown on R2A agar (DIFCO Laboratories). Several colonies from a culture plate were suspended in 100 µL of water. The mixture was frozen and then thawed once. The 16S rRNA gene sequences were amplified by PCR using a commercial kit according to the manufacture's instructions (Perkin Elmer™ Life Scienes, Boston, Mass.) with primers HK12 (5'-GAGTTTGATCCTGGCTCAG-3') (SEQ ID NO:3) and HK13 (5'-TACCTTGTTACGACTT-3') (SEQ ID NO:4). PCR was performed in an Applied Biosystems GeneAmp® 9600 (Foster City, Calif.). The samples were incubated for 5 min at 94° C. and then cycled 35 times at 94° C. for 30 sec, 55° C. for 1 min, and 72° C. for 1 min. The amplified 16S rRNA genes were purified using a commercial kit according to the manufacturer's instructions (QIAquick PCR Purification Kit, Qiagen, Valencia, Calif.) and sequenced on an automated ABI sequencer. The sequencing reactions were initiated with primers HK12, HK13, and HK14 (5'-GTGC-CAGCAGYMGCGGT-3') (SEQ ID NO:5, where Y=C or T, M=A or C). The 16S rRNA gene sequence of each isolate was used as the query sequence for a BLAST search (Altschul et al., *Nucleic Acids Res.* 25:3389–3402 (1997)) of GeneBank® for similar sequences.

A 16S rRNA gene of strain AN12 was sequenced and compared to other 16S rRNA sequences in the GenBank® sequence database. The 16S rRNA gene sequence from strain AN12 was at least 98% similar to the 16S rRNA gene sequences of high G+C Gram positive bacteria belonging to the genus *Rhodococcus*.

EXAMPLE 2

Preparation of Genomic DNA for Sequencing and Sequence Generation

Genomic DNA preparation. *Rhodococcus erythropolis* AN12 was grown in 25 mL NBYE medium (0.8% nutrient broth, 0.5% yeast extract, 0.05% Tween-80) till mid-log phase at 37° C. with aeratin. Bacterial cells were centrifuged at 4,000 g for 30 min at 4° C. The cell pellet was washed once with 20 mL 50 mM $Na_2CO_3$ containing 1 M KCl (pH 10) and then with 20 mL 50 mM NaOAc (pH 5). The cell pellet was gently resuspended in 5 mL of 50 mM Tris-10 mM EDTA (pH 8) and lysozyme was added to a final concentration of 2 mg/mL. The suspension was incubated at 37° C. for 2 h. Sodium dodecyl sulfate was then added to a final concentration of 1% and proteinase K was added to 100 µg/mL final concentration. The suspension was incubated at 55° C. for 5 h. The suspension became clear and the clear lysate was extracted with equal volume of phenol:chloroform:isoamyl alcohol (25:24:1). After centrifuging at 17,000 g for 20 min, the aqueous phase was carefully removed and transferred to a new tube. Two volumes of ethanol were added and the DNA was gently spooled with a sealed glass Pasteur pipette. The DNA was dipped into a tube containing 70% ethanol, then air dried. After air drying, DNA was resuspended in 400 µL of TE (10 mM Tris-1 mM EDTA, pH 8) with RNaseA (100 µg/mL) and stored at 4° C.

Library construction. 200 to 500 µg of chromosomal DNA was resuspended in a solution of 300 mM sodium acetate, 10 mM Tris-HCl, 1 mM Na-EDTA, and 30% glycerol, and sheared at 12 psi for 60 sec in an AeorMist™ Downdraft Nebulizer chamber (IPI Medical products, Chicago, Ill.). The DNA was precipitated, resuspended, and treated with Bal31 nuclease (New England Biolabs, Beverly, Mass.). After size fractionation by 0.8% agarose gel electrophoresis, a fraction (2.0 kb or 5.0 kb) was excised, cleaned, and a two-step ligation procedure was used to produce a high titer library with greater than 99% single inserts.

Sequencing. A shotgun sequencing strategy approach was adopted for the sequencing of the whole microbial genome (Fleischmann et al., *Science*, 269:496–512 (1995)).

Sequence was generated on an ABI Automatic sequencer using dye terminator technology (U.S. Pat. No. 5,366,860; EP 272,007) using a combination of vector and insert-specific primers. Sequence editing was performed in either DNAStar (DNA Star Inc., Madison, Wis.) or the Wisconsin GCG program (Wisconsin Package Version 9.0, Genetics Computer Group (GCG), Madison, Wis.) and the CONSED package (version 7.0). All sequences repesent coverage at least two times in both directions.

EXAMPLE 3

Identification of oxd ORF from Strain AN12

The oxd ORF was identified by conducting BLAST (Basic Local Alignment Search Tool; Altschul et al., *J. Mol. Biol.*, 215:403–410 (1990)) searches for similarity to sequences contained in the BLAST "nr" database (comprising all non-redundant (nr) GenBank® CDS translations, sequences derived from the 3-dimensional structure Brookhaven Protein Data Bank, the SWISS-PROT protein sequence database, EMBL, and DDBJ databases). The sequences obtained in Example 2 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Altschul et al., *Nucleic Acid Res.*, 25:3389–3402 (1997)) provided by the NCBI.

The results of the BLAST comparison are given in Table 1 which summarize the sequences to which they have the most similarities. Results from the BLAST analysis indicated that the aldoxime dehydratase from *Rhodococcus erythropolis* strain AN12 (SEQ ID NOs:1 and 2) shared homology to a phenylacetaldoxime dehydratase from *Bacillus sp.* OxB-1 (AB028892) (percent identity=31%, percent similarity=50%, E-value 5e-46). Table 1 displays data based on the BLAST algorithm with values reported in expect values. The Expect value estimates the statistical significance of the match, specifying the number of matches, with a given score, that are expected in a search of a database of this size absolutely by chance.

Table 1 summarizes the BLASTX results for the ORF that corresponds to the oxd gene and that was identified by genome sequencing of *Rhodococcus erythropolis* strain AN12.

TABLE 1 oxd from *Rhodococcus erythropolis* AN12.

| ORE | Gene | Similarity Identified | % Identity[a] | % Similarity[b] | E-value[c] | Citation |
|---|---|---|---|---|---|---|
| 1 | oxd | dbj = BAA90461.1 = (AB028892) phenylacetaldoxime dehydratase [Bacillus sp. OxB-1] | 31 | 50 | 5e-46 | Kato et al., Biochemistry 39:800–809 (2000) |

[a]%Identity is defined as percentage of amino acids that are identical between the two proteins.
[b]%Similarity is defined as percentage of amino acids that are identical or conserved between the two proteins.
[c]Expect value. The Expect value estimates the statistical significance of the match, specifying the number of matches, with a given score, that is expected in a search of a database of this size absolutely by chance.

EXAMPLE 4

Cloning of the Gene for Aldoxime Dehydratase from *R. ertyhropolis* Strain AN12

This Example describes cloning of oxd from *R. erythropolis* strain AN12. The oxd gene was amplified from stain AN12 by PCR and then cloned into an *E. coli* expression vector.

Primers ALD-F (5'-ATGGAATCTGCAATCGGTGAA-CAT-3') (SEQ ID NO:6) and ALD-R (5'-GTGCGCGGCG-GTGGTCACCGCGTC-3') (SEQ ID NO:7) were used in PCR reactions to amplify a 1,058 bp fragment (SEQ ID NO:3) from strain AN12 genomic DNA. The PCR reaction was performed with AMPLITAQ® DNA polymerase (Applied Biosystems) in buffer supplied by the manufacturer (GENEAMP® 10×PCR Buffer II) containing dNTPs (200 μM of each), primers (ALD-F and ALD-R), and AN12 DNA (3 μg). The reactions were incubated in an Applied Biosystems GENEAMP® 9600 for 25 cycles at 94° C. for 30 sec, 55° C. for 1 min and 72° C. for 1 min. The amplified DNA was analyzed by electrophoresis in 0.8% agarose using 1×TAE buffer and then purified using a QIAquick PCR Purification Kit according to the manufacturer's instrucitions (Qiagen).

The PCR product was inserted into plasmid pTrcHis2-TOPO™ using a commercial cloning kit according to the manufacturer's instructions (Invitrogen). Ligated DNA was transformed into MAX Efficiency™ DH5α® competent *E. coli* cells (Invitrogen) and plated onto LBamp agar (LB agar with 50 μg/mL ampicillin) and incubated at 37° C. overnight. Several transformants were patched onto fresh LBamp agar and inoculated into 3 mL of LB medium with ampicillin (50 μg/mL) and grown overnight in a 37° C. rotary drum. The plasmid DNA from each of these tranformants was extracted using the Qiagen Spin Miniprep kit. Each plasmid was digested in separate reactions with EcoRV (Promega, Madison, Wis.) or PvuII (Promega) and analyzed by electrophoresis in a 1% TAE agarose gel. Plasmid pMC552 had EcoRV restriction fragments (4503 bp, 937 bp) and PvuII restriction fragments (3858 bp, 1489 bp, 93 bp) that corresponded to the forward orientation (i.e., orientation that would allow expression of oxd) of the oxd insert. Plasmid pMC553 had EcoRV restriction fragments (3834 bp, 1606 bp) and PvuII restriction fragments (4687 bp, 568 bp, 93 bp) that corresponded to the reverse orientation (i.e., orientation that would prevent expression of oxd) of the oxd insert.

EXAMPLE 5

Expression of oxd in *E. coli*

This example describes how expression of the cloned *Rhodococcus* AN12 oxd in *E. coli* resulted in conversion of acetaldoxime to acetonitrile.

*E. coli* strains DH5α(pMC552) and DH5α(pMC553) were inoculated into 25 mL of M9 medium supplemented with 0.4% caseamino acids, 0.4% glycerol, and 50 μg/mL ampicillin. The cultures were incubated 18 hours at 30° C. with reciprocal shaking. The cells were harvested by centrifugation and resuspended in 25 mL of M9 medium supplemented with 100 ppm acetaldoxime, 0.4% glycerol, 0.1 mM IPTG and 50 μg/mL of ampicillin. The cultures were incubated at 30° C. with reciprocal shaking. The starting optical densities ($OD_{600}$) of the cultures were approximately 0.9. Samples were removed at various times, filter sterilized using 0.2 μm Acrodisc® GHP membrane filters (Pall Life Science, Ann Arbor, Mich.) and analyzed for acetonitrile by GC/FID.

The samples were analyzed using a HP6890 GC with a Supelco PTA-5 column (Sigma-Aldrich). Samples (1 μL) were injected with a 50:1 split. The injector and detector were operated at 300° C. The GC column conditions were (1) the oven temperature was increase from 60° to 275° C. in 30 minutes and (2) the flow rate was 1.5 mL/minute. Under these conditions, the retention time of acetonitrile was 5.6 minutes.

The data in Table 2 indicated that *E. coli* strain DH5α (pMC552) produced acetonitrile when exposed to acetaldoxime but that strain DH5α(pMC553) failed to do so.

TABLE 2

Transformation of acetaldoxime by DH5α(pMC552) to produce acetonitrile

| | Concentration of acetonitrile (ppm) | |
|---|---|---|
| Time(hrs) | DH5α(pMC552) | DH5α(pMC553) |
| 0 | 0 | 0 |
| 24 | 26.91 | 0 |
| 48 | 24.96 | 0 |
| 89 | 46.62 | 0 |

---

What is claimed is:

1. An isolated nucleic acid molecule encoding an aldoxime dehydratase, as set forth in SEQ ID NO:2; or an isolated nucleic acid fragment that is completely complementary to said isolated nucleic acid molecule.

2. A chimeric gene comprising the isolated nucleic acid molecule of claim 1 operably linked to a suitable regulatory sequence.

3. A transformed host cell comprising the chimeric gene of claim 2.

4. The transformed host cell of claim 3 wherein the host cell is selected from the group consisting of bacteria, yeast, filamentous fungi, algae, and green plants.

5. The transformed host cell of claim 4 wherein the host cell is selected from the group consisting of *Aspergillus*, *Trichoderma*, *Saccharomyces*, *Pichia*, *Candida*, *Hansenula*, *Salmonella*, *Bacillus*, *Acinetobacter*, *Zymomonas*, *Agrobacterium*, *Erythrobacter*, *Chlorobium*, *Chromatium*, *Flavobacterium*, *Cytophaga*, *Rhodobacter*, *Rhodococcus*, *Streptomyces*, *Brevibacterium*, *Corynebacteria*, *Mycobacterium*, *Deinococcus*, *Escherichia*, *Erwinia*, *Pantoea*, *Pseudomonas*, *Sphihgomonas*, *Methylomonas*, *Methylobacter*, *Methylococcus*, *Methylosinus*, *Methylomicrobium*, *Methylocystis*, *Methylobacterium*, *Alcaligenes*, *Synechocystis*, *Synechococcus*, *Anabaena*, *Thiobacillus*, *Methanobacterium*, *Klebsiella*, *Myxococcus*, and *Staphylococcus*.

6. The transformed host cell of claim 4 wherein the host cell is selected from the group consisting of *Spirulina*, *Haemotacoccus* and *Dunalliela*.

7. The transformed host cell of claim 4 wherein the host cell is selected from the group consisting of soybean, rapeseed, pepper, sunflower, cotton, corn, tobacco, alfalfa, wheat, barley, oats, sorghum, rice, *Arabidopsis*, cruciferous vegetables, melons, carrots, celery, parsley, tomatoes, potatoes, strawberries, peanuts, grapes, grass seed crops, sugar beets, sugar cane, beans, peas, rye, flax, hardwood trees, softwood trees, and forage grasses.

8. An isolated nucleic acid molecule as set forth in SEQ ID NO:1.

* * * * *

UNITED STATES PATENT AND TRADEMARK OFFICE
CERTIFICATE OF CORRECTION

PATENT NO. : 7,057,030 B2
APPLICATION NO. : 10/387094
DATED : June 6, 2006
INVENTOR(S) : Bramucci Michael G., Chen Mario W. and Nagarajan Vasantha It is certified that error appears in the above-identified patent and that said Letters Patent is hereby corrected as shown below:

Col. 31, lines 55-58, should read, An isolated nucleic acid molecule encoding an aldoxime dehydratase, as set forth in SEQ ID NO:2; or an isolated nucleic acid fragment that it completely complementary over its full length to said isolated nucleic acid molecule.

Signed and Sealed this

Fifteenth Day of August, 2006

JON W. DUDAS
*Director of the United States Patent and Trademark Office*